United States Patent [19]
Rousseau et al.

[11] Patent Number: 6,081,326
[45] Date of Patent: Jun. 27, 2000

[54] DEVICE FOR AUTOMATIC READING OF AN IDENTIFICATION CODE CARRIED BY TUBULAR CONTAINERS

[75] Inventors: Alain Rousseau; Jean Francois Gelin, both of Francaise, France

[73] Assignee: Diagnostica Stago, France

[21] Appl. No.: 09/242,306

[22] PCT Filed: Jun. 11, 1998

[86] PCT No.: PCT/FR98/01222

§ 371 Date: Feb. 12, 1999

§ 102(e) Date: Feb. 12, 1999

[87] PCT Pub. No.: WO98/58262

PCT Pub. Date: Dec. 23, 1998

[30] Foreign Application Priority Data

Jun. 16, 1997 [FR] France ................................ 97 07752

[51] Int. Cl.[7] .............................. G01N 1/10; G01N 35/02
[52] U.S. Cl. ........................... 356/246; 356/440; 422/65; 422/100; 422/104; 436/47
[58] Field of Search ........................... 356/246, 244, 356/440; 422/63, 65, 100, 103, 104, 64; 436/43, 47

[56] References Cited

U.S. PATENT DOCUMENTS 4,729,661   3/1988   Bell ........................................ 356/246

Primary Examiner—Hoa Q. Pham
Attorney, Agent, or Firm—William A. Drucker

[57] ABSTRACT

The invention concerns a device for the automatic reading of an identification code carried by tubular containers (T) arranged in racks, comprising rotating means (M) acting by friction on the tube (T) cylindrical wall through an orifice (OF) provided in one of the two vertical walls ($FL_1$, $FL_2$) which extend longitudinally relative to the displacement axis of the racks (R) to cause the tube to rotate during the code reading phase. The invention is useful for identifying sample tubes when they are introduced into a blood analyzer.

16 Claims, 2 Drawing Sheets

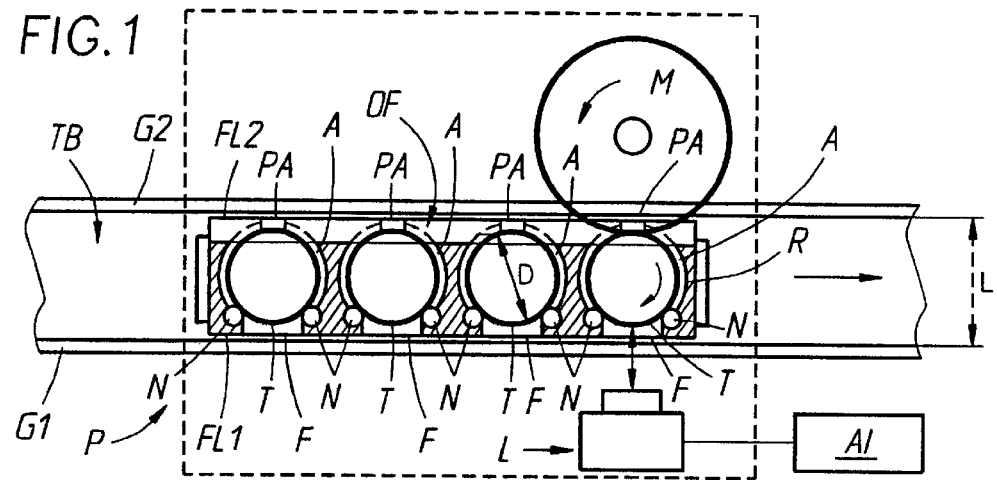
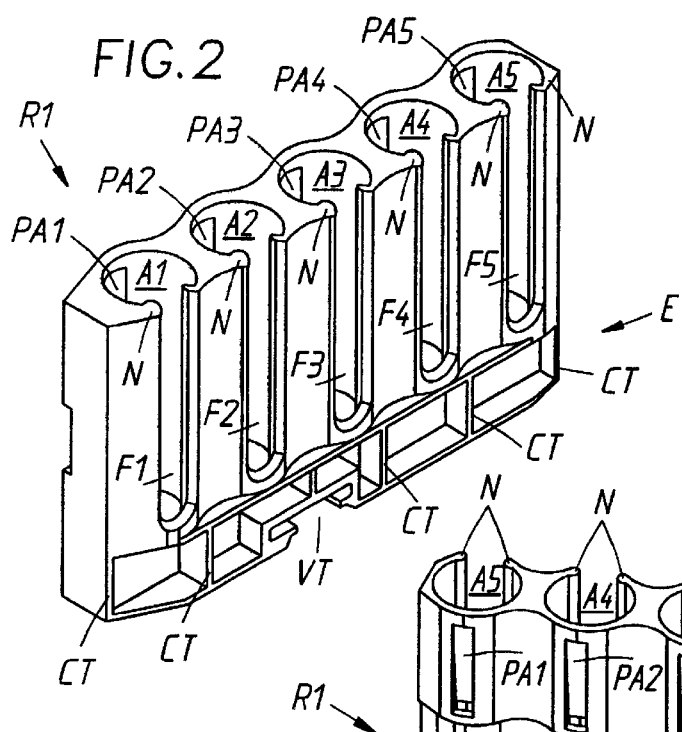
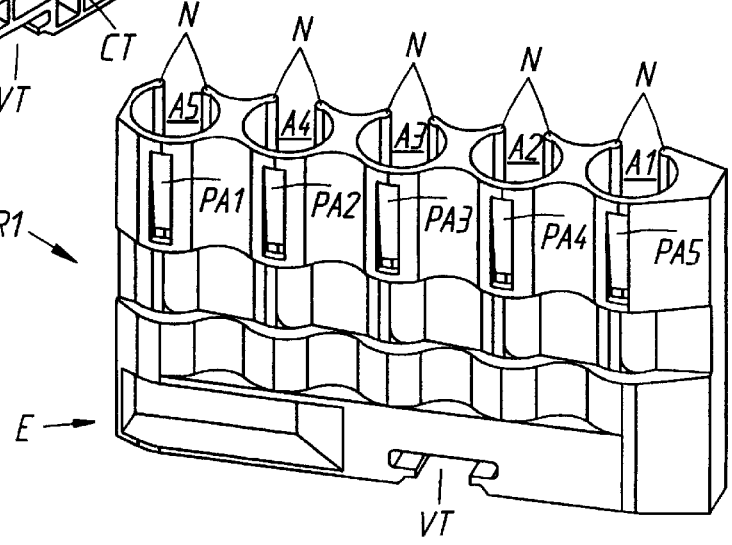

DEVICE FOR AUTOMATIC READING OF AN IDENTIFICATION CODE CARRIED BY TUBULAR CONTAINERS

BACKGROUND OF THE INVENTION

1. Field of the Invention

This invention relates to a device for the automatic reading of an identification code carried by tubular containers placed in filing boxes or carrier units circulating on a distribution chain.

It applies notably, though not exclusively, to the automatic identification of tubes of samples, e.g. of blood, being introduced into an automated analysis system.

It also relates to a filing box or carrier unit specially designed to enable said reading.

2. Description of the Prior Art

Generally, it is known that the blood samples to be analyzed in a modern automated analysis system are arranged in test tubes, usually in glass or plastic, sealed by a stopper. These tubes are identified by an identification code carried by a label adhering to the cylindrical wall of the tube. This identification code, e.g. a bar code, is designed to be readable remotely by an e.g. optoelectronic reading unit.

The tubes, fitted with their identification labels, are arranged in carrier units especially designed to be capable of being borne along by the conveyors equipping the automated analysis system.

In order for the automated system to be able to identify the samples, it has been proposed that, at the entrance to the automated system, manual or semi-automated entry be performed of the tube identification data, of the carrier units and of the positions of the tubes within the carrier units. However, this type of entry requires the presence of an operator and involves a high risk of error.

To remedy these drawbacks, it was therefore proposed that an automatic data reading system be placed along the path of the automaton's supply conveyor. However, to achieve such a result one must solve the problem stemming from the fact that the angular position of the tubes is undefined and that the label carried by the tube is therefore not always properly oriented in relation to the reader.

In order to solve this problem, a reader was therefore provided with a means enabling the tube to be rotated during the reading phase.

Thus, the reader disclosed in European patent No. 0,479,622 uses a rotary drive element designed to grasp the stopper of the tube at the end of a downward translation.

Experience has shown that this solution has a certain number of drawbacks:

- it is relatively complex and uses complicated and costly means,
- for each read operation, it requires a relatively long stoppage time and does not enable high outputs to be achieved,
- it requires the use of stoppers specially designed for this purpose.

OBJECT OF THE INVENTION

The main object of this invention is to remedy the preceding disadvantages, particularly to provide to this end a device for the reading of identification codes borne on a medium affixed to the cylindrical wall of the specimen tubes arranged in a carrier unit transported by a conveyor of a distribution device.

SUMMARY OF THE INVENTION

Accordingly, this device is characterized in that it uses a rotary drive means acting by friction on the cylindrical wall of the tube, through an opening provided in one of the two vertical walls extending longitudinally in relation to the axis of travel of the carrier units, so as to rotate the tubes about themselves during the code reading phase but also to enable inspection by camera from which certain information can be deduced about the specimen contained in the tube, such as:

hematocrit, tube filling level, quality of the sample (hemolysed plasma, etc.).

Advantageously, the drive means can consist of a small roller or endless belt made in a material with a high coefficient of friction and arranged so as to bear against the cylindrical wall of the tube when the latter is in the reading zone.

Likewise, the aforesaid opening can extend over the entire length of said lateral wall so as to enable the drive means to successively come into contact with the tubes without requiring any alternating transverse motion of said means.

BRIEF DESCRIPTION OF THE DRAWINGS

Further features and advantages of the invention will be apparent from the embodiments of the invention described, by way of non-limiting examples, in reference to the corresponding accompanying drawings in which:

FIG. 1 is a schematic representation enabling the operating principle of the reading device to be illustrated;

FIGS. 2 and 3 are side perspective views of a monobloc carrier unit in molded plastic;

DESCRIPTION OF THE PREFERRED EMBODIMENTS

Figure 4:
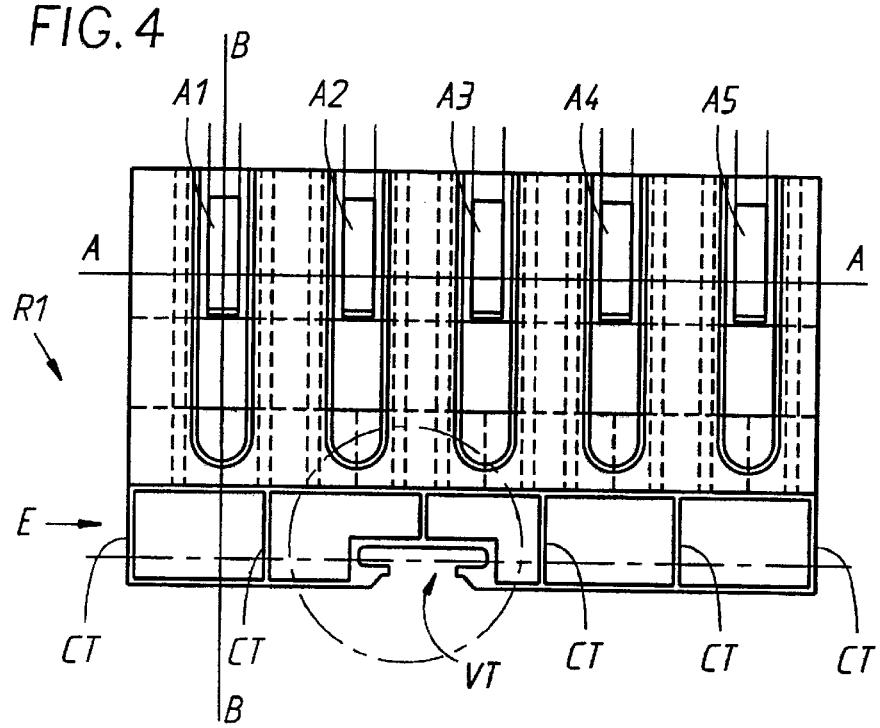
FIG. 4 is a sectional view of the carrier unit according to the longitudinal vertical plane of symmetry.

In the example illustrated in FIG. 1 which schematically represents a top view, with a partial horizontal cutaway, of a station P for the identification of specimen tubes T contained in a carrier unit R, of a distribution system associated e.g. with an automated analysis system.

In this example, the carrier unit R comes in the form of an alveolar structure in molded plastic, inscribed within a rectangular parallelepiped of width L slightly greater than the diameter D of the tubes T. It comprises two open-worked vertical longitudinal sides $FL_1$, $FL_2$ between which are formed five vertical cylindrical alveolar cells A intended to house five respective specimen tubes T.

The openings made in the side $FL_1$ extend over a large part of the height of the alveolar cells A and constitute windows F intended to enable both the optical reading of the identification codes borne on the cylindrical walls of the tubes T and the inspection of the contents of the tube.

The openings made in the side $FL_2$ comprise a slit-shaped opening OF which extends over the entire length of the carrier unit R.

The carrier unit R rests, by way of its base, on a belt-type slide rail TB comprising e.g. a belt fitted with abutments, is guided laterally by two slide rails $G_1$, $G_2$ and is driven by a belt fitted with tappets called a "conveying" belt. This conveyor is actuated by a step-by-step motor (or a continuously operating motor if it is automatically controlled), passes through the identification station P to bring the carrier units R fitted with their tubes T to the mouth of the automated analysis system.

The identification station P, materialized in this instance by rectangle drawn in broken lines, comprises:
- on the one hand, an optoelectronic reading device L (e.g. a video camera associated with an image analyzer AI or reader of identification code such a bar code), located on one side of the conveyor TB, so as to be able to record the image of the cylindrical wall of each of the tubes T and of their content every time the window F, which enables the tube to be seen, is situated within the field of the reading device L, and
- on the other hand, a drive device consisting in this instance of a knurling wheel M, in a resilient material such as rubber, rotated by an electric motor; this knurling wheel M of vertical axis is located at the level of the reading device, on the other side of the conveyor TB in order to be able to engage itself in the longitudinal opening OF of the carrier unit R so as to successively come and bear against the cylindrical wall of the tubes T and thus drive them in rotation.

To facilitate this rotation, and to enable good positioning of the cylindrical side of the tube T in relation to the reading device L, the alveolar cells A comprise two vertical bearing elements, in this instance vertical ribs N, which are protrusions extending to both sides of a plane of symmetry of the window F, as well as an elastically deformable bearing part PA situated on the alveolar cell A side opposite the window F; this bearing part PA is intended to hold the tube T applied against the rounded edges of the carrier unit, therefore in a position perfectly centered in relation to the window F.

The rounded edges could be replaced by small rotating rollers of vertical axis so as to reduce, insofar as possible, the frictional forces susceptible of opposing the rotation of the tubes T and to limit catching of labels, especially when the latter are badly stuck on.

When the edge of a label is slightly unstuck, an unstuck portion can become stuck back when the tube is rotated. The ribs are therefore positioned so as to avoid the sticking phenomenon.

It is obvious that, by way of these relatively simple, inexpensive and yet efficient arrangements, it becomes possible to achieve reliable identification of the tubes T, of the position of these tubes within carrier units R as well as identification of the carrier units, e.g. by a reading of a code identifying the carrier unit by the same reading device L.

Likewise, continuous inspection of the tube is made easy without risking mixing the cells (globules) and plasma separated beforehand by centrifugation.

Figure 5:
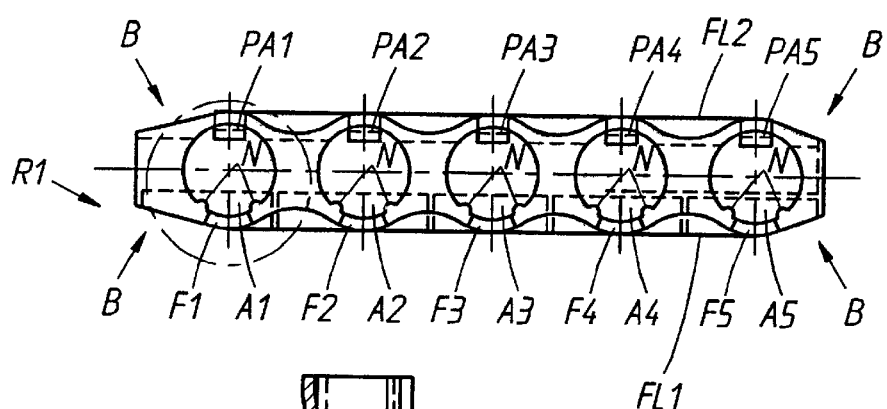
FIG. 5 is a horizontal sectional view along A/A of FIG. 4.
Figure 6:
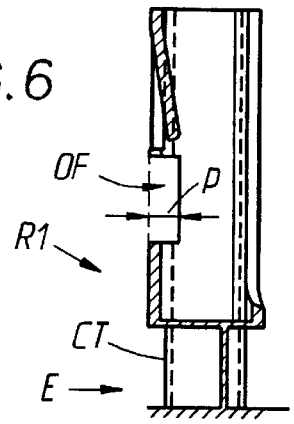
FIG. 6 is a vertical sectional view along B/B of FIG. 4.

The carrier unit $R_1$ represented in FIGS. 2 to 6 is of a structure similar to the one previously described.

However, in this instance, the vertical edges B of the parallelepiped shape, which are situated at the two ends, are beveled.

The lower part of the carrier unit $R_1$ comprises a seat E of transverse profile in the shape of a tilted "H" and which comprises a series of transversal partitionings CT (stiffeners) capable of facilitating centrifugation.

In its central region, the seat E is fitted with a rib delimiting a transversal volume VT of substantially "C"-shaped or dovetail-shaped cross section, intended to cooperate with a guide rail of complementary e.g. "T"-shaped cross-section.

The upper part of the carrier unit $R_1$ comprises, in this instance, five vertical cylindrical alveolar cells $A_1$ to $A_5$ open at the level of the upper side of the carrier unit, the diameter of these alveolar cells $A_1$ to $A_5$ being slightly greater than the diameter of the tubes and slightly less than the width of the carrier unit $R_1$.

On the side of side $FL_1$, these alveolar cells $A_1$ to $A_5$ open outwards by way of oblong windows $F_1$ to $F_5$ which extend from the upper side of the unit to the level of the seat.

These windows $F_1$ to $F_5$ are intended to enable reading of the identification codes inscribed on the cylindrical wall of the tubes or on labels stuck to these walls.

On the side of side $FL_2$, the carrier unit $R_1$ comprises an opening of rectangular section $OF_1$ which extends horizontally, at mid-height of the carrier unit $R_1$, from one end of said unit to the other. The depth p of this opening is provided such that one portion of the wall of the tubes is bared and can thus cooperate with a rotary drive means of the type of the knurling wheel M represented in FIG. 1.

As in the example previously described, the alveolar cells $A_1$ to $A_5$ comprise, on both sides of the windows $F_1$ to $F_5$, rounded surfaces N (furrowed surfaces) against which the tubes come to bear, preferably at a tangent, and can turn while solving the previously mentioned problem or partial unsticking of the label.

Opposite each of these rounded surfaces N is provided a flexible tab $PA_1$ to $PA_5$ extending obliquely slightly into the interior volume of the corresponding alveolar cell $A_1$ to $A_5$ so as to maintain the tube applied against the rounded surfaces irrespective of existing standard diameter.

This tab PA1 to PA5 is cast integral with the rest of the carrier unit.

We claim:

1. Carrier unit intended to house at least one tubular container having a cylindrical wall which bears an identification code intended to be read remotely by an optoelectronic reader, wherein said carrier unit is in the form of an alveolar structure comprising first and second vertical longitudinal walls between which is formed at least a vertical cylindrical alveolar cell intended to house said tubular containers, said first longitudinal side being provided with at least a window intended to enable both an optical reading of the identification codes and an optical inspection of the contents of the tubular container, whereas said second longitudinal side comprises a slit-shaped opening extending over the entire length of the carrier unit.

2. Carrier unit as claimed in claim 1, which is cast in one single molded piece.

3. Carrier unit as claimed in claim 2, wherein the alveolar cell comprises two rounded vertical bearing elements, and an elastically deformable bearing part, protruding on the alveolar cell side opposite the window.

4. Carrier unit as claimed in claim 3, wherein the said bearing elements consist of rotary rollers of vertical axis.

5. Carrier unit as claimed in claim 3, wherein the bearing part consists of a slightly oblique flexible tab cast integral with said carrier unit.

6. Carrier unit as claimed in claim 3, wherein the said bearing elements consist of furrowed surfaces enabling the tubular container to be rotated.

7. Device for automatically reading an identification code carried by a cylindrical wall of a tubular container having a coaxial vertical axis of rotation and placed inside a carrier unit provided with first and second parallel vertical walls, said carrier being transported by a conveyor having an axis of travel parallel to said vertical walls and passing through a reading zone, said first vertical wall being provided with an elongated opening which extends in a direction parallel to said axis of travel and said second vertical wall having at least a window facing said cylindrical wall, said device comprising a rotary drive means having a friction means which comes in tangential contact on said cylindrical wall through said elongated opening when the carrier unit is in said reading zone, for imparting to said tubular container a rotating motion about said axis of rotation, reading means being provided for reading said identification code through said window while the tubular container is rotating about said axis in said reading zone.

8. Device as claimed in claim 7, wherein said rotary drive means consists of a roller made in a material with a high coefficient of friction which come into contact on said cylindrical wall when said tubular container is in said reading zone.

9. Device as claimed in claim 7, wherein the said opening can extend over the entire length of said vertical wall for enabling the drive means to successively come into contact with the receptacles without requiring any alternating transverse motion of said means.

10. Device as claimed in claim 7, wherein the carrier unit has a side opposite said opening provided with a series of windows enabling the optical reading of identification codes carried by the containers and an optical inspection of the contents of said containers.

11. Device as claimed in claim 7, wherein the carrier unit comes in the form of an alveolar structure of molded material, inscribed within a rectangular parallelepiped comprising two open-worked vertical longitudinal sides between which are formed vertical cylindrical alveolar cells intended to house specimen tubes, the openings made in one of said sides constituting windows intended to enable both the optical reading of the identification codes borne on the cylindrical walls of the said tubes and an inspection of the contents thereof, whereas the openings made in the side comprise a slit-shaped opening which extends over the entire length of the carrier unit.

12. Device as claimed in claim 11, wherein the alveolar cells comprise two vertical and rounded bearing elements, and an elastically deformable bearing part situated on the alveolar cell side opposite the said window.

13. Device as claimed in claim 12, wherein the said bearing elements consist of rotary rollers of vertical axis enabling one of said tubes to be rotated.

14. Device as claimed in claim 12, wherein the bearing part consists of a slightly oblique flexible tab cast integral with the rest of the carrier unit.

15. Device as claimed in claim 12, wherein the said bearing elements consist of furrowed surfaces enabling the tube to be rotated.

16. Device as claimed in claim 7, wherein said rotary drive means consist of an endless belt having a high coefficient of friction, on which said tubular container come into contact when said tubular container is in a reading zone.

* * * * *